United States Patent [19]

Pieters et al.

[11] 4,451,356

[45] May 29, 1984

[54] CATALYTIC DEHYDROXYLATION OF PHENOLS

[75] Inventors: Wim J.M. Pieters, Morristown, N.J.; Gerard M. Prilutski, New Castle, Del.

[73] Assignee: Exxon Research and Engineering Co., Florham Park, N.J.

[21] Appl. No.: 371,455

[22] Filed: Apr. 23, 1982

Related U.S. Application Data

[63] Continuation-in-part of Ser. No. 218,526, Dec. 22, 1980, abandoned.

[51] Int. Cl.$^3$ .................... C10G 17/00; C10G 45/00; C07C 1/20
[52] U.S. Cl. .................................. 208/263; 585/469
[58] Field of Search ................... 208/16, 263; 585/469

[56] References Cited

U.S. PATENT DOCUMENTS 1,430,585 10/1922 Ramage .
2,921,023 1/1960 Holm .
4,062,904 12/1977 Schmerling .

FOREIGN PATENT DOCUMENTS 639762 12/1936 Fed. Rep. of Germany .
378501 8/1932 United Kingdom .
395370 7/1933 United Kingdom .
403708 12/1933 United Kingdom .

OTHER PUBLICATIONS

Org. Khim. vol. 13, No. 12, p. 2622, Dec. 1977.
"Sulphide Catalysts, Their Properties and Applications", Weisser and Landa (1973) p. 157.
"Coal Hydrogenation Vapor Phase", E. E. Donath, Advances in Catalysis, vol. VIII, 251 (1956).
"Catalytic Hydrogenation of Phenols", Shuikin and Erivanskaya: Russian Chemical Reviews, vol. 29, 309-320 (1960).
"Production of Toluene from Coal Tar", Cawley et al., J. Inst. Petrol. 32, 660-683 (1946).
"Catalytic Hydrogenation of Model Nitrogen, Sulfur, and Oxygen Compounds", Rollmann: Journal of Catalysis 46, 243-252 (1977).

*Primary Examiner*—Delbert E. Gantz
*Assistant Examiner*—Helane E. Maull
*Attorney, Agent, or Firm*—Robert J. North

[57] ABSTRACT

Phenolic compounds are dehydroxylated in the vapor phase by contacting with a reducing atmosphere substantially comprising hydrogen sulfide as the reducing agent in the presence of a sulfur-tolerant metal sulfide catalyst. The additional presence of hydrogen gas helps to desulfurize the catalyst and maintain catalytic activity. The process is useful in the treatment of phenolic naphtha fractions present in coal liquids, produced by pyrolysis or direct coal liquefaction.

16 Claims, No Drawings

CATALYTIC DEHYDROXYLATION OF PHENOLS

CROSS-REFERENCE TO RELATED APPLICATIONS

This application is a continuation-in-part application of Ser. No. 218,526, filed Dec. 22, 1980 now abandoned.

BACKGROUND OF THE INVENTION

1. Field of the Invention

This invention relates to a new process for dehydroxylating phenolic compounds wherein a mixture of phenolic compounds in vapor form hydrogen sulfide as the reducing agent, and a small amount of hydrogen gas to maintain catalyst activity, is contacted with a sulfur tolerant metal sulfide catalyst at elevated temperature.

2. Brief Description of Disclosures in The Art

Coal will be one of the major sources for the future supply of liquid fuels in the future and an intensive effort is being undertaken in the development of coal liquefaction technology.

The naphtha fraction (atmospheric boiling point—room temperature to 420° F.) produced from coal liquids by current technology contains substantial amounts of phenolic compounds, mainly as phenol, cresols, and xylenols. These phenolic compounds are primarily responsible for the corrosive nature and instability of the material and present a serious obstacle to the subsequent refining of the naphtha fraction for producing automotive, industrial or residential heating fuel. Modification of these undesirable properties of the coal liquid naphtha fraction or removal thereof would greatly enhance its processing and refining utility. In this context, new processes for treating the phenolic portion of the naphtha fraction in coal liquids are constantly being evaluated to develop a suitable commercial process.

One process that has been seriously considered is the treatment of the phenolic portion of the naphtha fraction by vapor-phase dehydroxylation using hydrogen gas as the primary reducing agent in the presence of a suitable hydrogenation catalyst. However, the use of hydrogen gas as the primary reducing agent is expensive and significantly adds to the overall cost of the process. Other gaseous reducing agents that would be less expensive and more readily available would significantly increase the applicability of a dehydroxylation process in general for treating the phenolic portion of the naphtha fraction in coal liquids.

The reference Org. Khim. Vol. 13, No. 12, p. 2622, December 1977, describes the high temperature conversion of benzaldehyde into trans-stilbene by contacting benzaldehyde in the vapor phase with gaseous hydrogen sulfide at elevated temperature. The reaction is described as being conducted in a quartz tube at 500° C. with repeated recycling of the initial compound through the reaction zone. However, no specific mention is made of the possibility of utilizing the process for dehydroxylating phenol type compounds, and further, no mention is made of the use of specific metal sulfide catalysts for such processes.

SUMMARY OF THE INVENTION

We have unexpectedly discovered that phenolic compounds can be efficiently dehydroxylated in the vapor phase by contacting with a reducing atmosphere substantially comprising gaseous hydrogen sulfide, as the reducing agent, in the presence of a sulfur tolerant metal sulfide catalyst under comparatively mild temperature conditions. In addition, hydrogen gas can also be preferably present, in small amounts, to maintain catalytic activity in a continuous process. The process can be particularly applied to the dehydroxylation of the phenolic portion of the naphtha fraction of a coal liquid, thus resulting in a noncorrosive stable naphtha fraction suitable for subsequent refinery operations for producing energy fuels.

In accordance with this invention, there is provided a process for dehydroxylating a phenolic compound comprising contacting said phenolic compound or mixture thereof in the vapor phase with a reducing atmosphere substantially comprising hydrogen sulfide, as the reducing agent, in the presence of a sulfur tolerant metal sulfide catalyst at elevated temperature.

Preferred embodiments include the phenolic compound as the phenolic fraction of a coal liquid; the catalyst selected from $MoS_x/Al_2O_3$, $FeS_x/Al_2O_3$, $WS_x/Al_2O_3$, $WS_x/NiS_x/Al_2O_3$, $NbS_x/Al_2O_3$, or mixtures thereof; and the hydrogen sulfide atmosphere containing a sufficient amount of hydrogen gas to maintain catalytic activity, particularly in a continuous process.

Further provided is the naphtha fraction of a coal liquid treated according to the above-described process.

DESCRIPTION OF THE INVENTION AND PREFERRED EMBODIMENTS

This invention process deals with vapor-phase catalyzed dehydroxylation and by the term "dehydroxylation" as applied herein to phenolic compounds, is meant the substitution of a hydrogen radical for a hydroxyl radical on the aromatic ring. For example, the dehydroxylation of phenol results in benzene and the dehydroxylation of the cresol results in toluene. With a dihydroxybenzene, one or both phenolic hydroxyl groups may be removed.

The overall reaction can be exemplified using unsubstituted phenol as the phenolic compound, and $H_2S$ as the reducing agent, by the following equation.

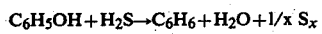

$$C_6H_5OH + H_2S \rightarrow C_6H_6 + H_2O + 1/x\, S_x$$

in which the products are benzene, water and elemental sulfur.

One aspect of the novelty in the process is that the reducing atmosphere in the process comprises substantially hydrogen sulfide but can also contain other gases, for example, carbon monoxide, carbon dioxide, ammonia, hydrogen and the like. By the term "substantially" is meant that hydrogen sulfide comprises from about 85 to 100 volume percent and preferably from 96 to 99.5 volume percent of the reducing agents in the reducing atmosphere. A preferred secondary gaseous component, when used, is hydrogen since it has been found that hydrogen gas maintains the stability of the catalyst, presumably by helping to remove sulfur which may be chemisorbed as a by-product of the catalyst surface during the catalytic dehydroxylation. The amount of hydrogen gas in the total process atmosphere can be about 0.001 to 15 volume percent, and preferably 0.5 to 4 volume percent of the total atmosphere. A further preferred embodiment is where hydrogen gas is present in just a sufficient amount to maintain the general catalyst activity for the dehydroxylation, particularly in a continuous process. By the term "catalytic activity" as used herein, is meant percent conversion and a preferred embodiment utilizes a sufficient amount of hydrogen gas such that the percent conversion remains approximately linear during a continuous process. Normally this will require about 0.001 to 15 volume percent of hydrogen gas, depending upon the particular process conditions and catalyst system employed.

The process is conducted such that the phenolic compound is in the vapor phase and this necessitates an elevated temperature sufficient for vaporization of the phenolic compound in the range of about 200° to 600° C. and preferably about 325° to 525° C.

The process can be conducted at a pressure from about 0.1 to 2.0 MPa and preferably about 0.1 MPa.

The space velocity of the total process vapor feed stream including phenolic compound, hydrogen sulfide and hydrogen, and optionally carrier gas, can be maintained at about 100 to 10,000 v/v/hr and preferably about 500 to 2,000 v/v/hr.

Catalysts which are applicable in the process are sulfur tolerant metal sulfides, and by the term "sulfur tolerant" as used herein, is meant metal sulfides generally of high surface area which are not deactivated by $H_2S$, and which, if deactivated by sulfur by-products, can be reversibly reactivated by contacting with hydrogen gas. The catalysts can be prepared by conventional methods. Representative examples include molybdenum sulfide, cobalt sulfide, tungsten sulfide, nickel sulfide, iron sulfide, niobium sulfide and mixtures thereof. A preferred metal sulfide in the process is niobium sulfide.

The catalyst can be used as is, being unsupported, or can be supported on a suitable support such as a difficultly sulfidable metal oxide and by this term is meant a metal oxide which, when contacted with hydrogen sulfide or sulfur or elevated temperature, is not significantly converted to a metal sulfide. Representative examples of suitable supports include gamma alumina, silica, silica-alumina and the like. Preferred support is gamma alumina and a preferred catalyst in the process is niobium sulfide deposited on alumina. Inert material, such as ceramic or glass beads, can also be utilized. The amount of metal sulfide deposited on the above-described support can be from about 2 to 25 wt. % metal sulfide on the support and preferably about 5 to 20 percent on said support.

By the term "phenolic compound" as used herein, is meant a hydroxy aromatic compound or mixture thereof. Included within the term are mono-, di-, and trihydroxy derivatives of benzene and naphthalenes, and substituted benzenes and naphthalenes such as mono-, di-, or trialkyl benzenes and mono-, di- and trialkyl benzenes and mono, di- and trialkyl naphthalenes. Representative examples include phenol; ortho-, meta-, and para-cresol; xylenols, including 1-hydroxy-2,6-dimethylphenol, and 2,4-dimethylphenol; 1-naphthol, 2-naphthol and the like. If preferred, a carrier gas can be used for the phenolic compound, such as cyclopentane for ease in introducing the phenolic compound into the process reaction feedstream.

Also included within the term "phenolic compounds" are $C_1$–$C_4$ alkoxyphenols such as methyl resorcinol and the like.

Further, included within the term "phenolic compound" is the phenolic naphtha fraction produced in coal liquids by pyrolysis or direct coal liquefaction which contains mainly phenol, cresols and xylenols.

Apparatus useful for carrying out the invention process may be any general type of vapor phase catalyst process apparatus such as fixed bed, fluid bed, down-flow, up-flow, horizontal-flow, moving bed, slurry and the like. The process can be run as a batch-wise or continuous operation. When utilizing a reducing atmosphere substantially comprising hydrogen sulfide, the metal sulfide catalysts described herein will generally lose catalyst activity in a gradual manner. This may be satisfactory in a batch-wise process, but a continuous process requires the presence of hydrogen gas to maintain catalyst activity over periods of time necessary in continuous operations.

A typical process run comprises mixing phenolic compound in the vapor phase with a mixture of hydrogen sulfide containing sufficient hydrogen gas to maintain catalyst activity and contacting the vaporized mixture with a sulfur tolerant metal sulfide catalyst at elevated temperature and under pressure and space velocity as specified herein. The formed dehydroxylated aromatic hydrocarbon product can be collected by conventional techniques such as condensation or distillation and the unreacted phenolic compound recycled back with any unused hydrogen sulfide from the exit gas feedstream. Sulfur and water, where formed, in the reactor can be removed by conventional techniques.

Percent conversion of phenolic compounds in the process is dependent on the exact process parameters chosen and can vary to a considerable degree. The conversions achieved in the following example of the invention are expressed as a rate of dehydroxylation of phenol to benzene and are in the order of $10^{-8}$ to $10^{-6}$ moles/gm-catalyst/second in the temperature range of 400° to 500° C. Facility for maximizing the percent conversion in the process will become obvious to one skilled in the art from this disclosure.

Also a subject of the invention is a phenolic naphtha fraction of a coal liquid which has been treated via catalytic dehydroxylation of the component phenolic compounds in the above process. The phenolic naphtha fraction can be treated, first separately by the subject process, and then recombined with the particular coal liquid. The process can be conducted such that a substantial amount of the corrosive nature of the phenolic fraction can be removed.

The following Example is illustrative of the best mode of carrying out the invention process, as contemplated by us, and should not be construed as being limitations on the scope or spirit of the instant invention.

EXAMPLE—BACKGROUND

1. Apparatus and Conditions

Phenol dehydroxylation runs were conducted in a fixed-bed microflow reactor. The reactor feed consisted of a mixture of five weight percent phenol in cyclopentane as a carrier solvent, and hydrogen sulfide. The liquid phenol mixture was fed to the reactor through a Milton Roy (D-19-60029-001) minipump. This solution was vaporized, mixed with cyclohexane and hydrogen sulfide and passed through the catalyst bed of the reactor, which was contained in a stainless steel tube measuring $\frac{1}{2}''\times 8''$. The reactor was heated by a furnace connected to a Data-Trak 5500/624A programmer-controller.

Process variables of the runs consisted of a liquid phenol/cyclopentane flow rate of 20 cc/hr., which is equivalent to a gas flow rate of 5 ml. of phenol/minute and 95 ml. cyclopentane/min., a hydrogen sulfide gas flow rate of 30 ml./min., and a diluent ($N_2$) flow rate of 125 ml./min., a reaction zone temperature of 400° C., a catalyst charge of 10 grams and operated at atmospheric pressure. The space velocity of the total gaseous feedstream was maintained at about 1,500 v/v/hr.

2. Catalyst Materials

The supported metal sulfide catalysts were prepared by first impregnating alumina, which was Harshaw Al-3945 (190 M²/g surface area/reforming grade gamma-alumina), with aqueous solutions of commercially available metal salts. The amount of solution used was sufficient to yield the weight percentages of metal sulfide on alumina listed on the Table.

After impregnation, the catalysts were dried overnight at 100° C. and calcined for four hours at 400° to 500° C. The calcined alumina catalysts were pressed at 20,000 lb./sq. inch into wafers which were subsequently crushed and screened to a size between 20 and 40 mesh.

For example, 85 ml. of an aqueous solution of 30 grams of ammonium molybdate were contacted with 100 grams of alumina. The wetted solid was heated at 100° C. overnight to complete drying. The resulting solid was ground and calcined at 400° C. for four hours resulting in a solid containing 11.15% Mo on alumina.

The catalysts were then sulfided in situ in the reactor into their corresponding sulfides, by contacting at 450° C., for thirty minutes, with a sulfiding gas flow of 15% $H_2S/H_2$ maintained at a gas flow rate of 100 cc/min.

3. Product Analysis

On-line analyses of the obtained product gas phase compositions were carried out with a PE-900 gas chromatograph. A sample loop of 0.5 cc was used to inject standard volume samples onto two $10' \times \frac{1}{8}''$ stainless steel columns in series. The first column was packed with SP-2100 and the second with SP-1000; these were programmed from 40° C. to 250° C.

Metal analysis, X-ray diffraction studies and carbon analysis of the catalysts were also performed.

EXAMPLE—PROCESS RUNS

Utilizing the above-described process conditions, the following catalysts, (with stated metal sulfide weight percentages) prepared as described above, were used in the phenol dehydroxylation runs at the respective listed temperatures. Phenol was used as a model compound for the phenolic component in the naphtha fraction in coal liquids, and reagent $H_2S$ gas was used on the reducing agent. The pressure used was at about 0.1 MPa, and the space velocity of the phenol component in the gaseous mixture in each case was 1 gm. phenol/10 gm-catalyst/hr. Volume ratio of phenol vapor to $H_2S$ in the gas mixture was about 1:30; temperature was 400° to 500° C. Rates for benzene formation, indicative of rate of phenol dehydroxylation, are also given in the following Table, after 20 minutes and 400 minutes of the respective runs.

TABLE

| Catalyst | Temperature (°C.) | $r = \frac{\text{Mole Benzene}}{\text{mole metal-sec}}$ (a) (at 200 min) | (at 400 min) |
|---|---|---|---|
| 17% $MoS_x/Al_2O_3$ | 420 | $5.1 \times 10^{-6}$ | $3.1 \times 10^{-6}$ |
| $CoS_x, MoS_x/Al_2O_3$ (c) | 400 | $0.83 \times 10^{-6}$ | $0.30 \times 10^{-6}$ |
| 10% $WS_x/Al_2O_3$ | 500 | $14.4 \times 10^{-6}$ | $10 \times 10^{-6}$ |
| 13% $WS_x$, 1% $NiS_x/Al_2O_3$ | 410 | $1.9 \times 10^{-6}$ | (b)— |
| 11% $FeS_x/Al_2O_3$ | 500 | $2.3 \times 10^{-6}$ | $1.8 \times 10^{-6}$ |
| 2.35% $NbS_x/Al_2O_3$ | 400 | $19 \times 10^{-6}$ | $10.7 \times 10^{-6}$ |
| 2.35% $NbS_x/Al_2O_3$ | 500 | $161 \times 10^{-6}$ | $134 \times 10^{-6}$ |

(a)Rate of dehydroxylation
(b)Total deactivation
(c)4% CoO, 12% $MoO_3$ prior to sulfiding It was observed that partial deactivation of the catalyst occurred in each case during the run and that total deactivation, after 400 minutes, was observed for the 13% $WS_x$, 1% $NiS_x/Al_2O_3$ catalyst. It was found that hydrogen gas regenerated the above catalysts when they became totally or partially deactivated despite sulfur loadings of over 15% at the end of the run; thus, catalyst deactivation under these conditions was demonstrated to be reversible. It is reasonably believed that by utilizing a hydrogen sulfide stream containing about 0.001 to 15 volume percent hydrogen gas, in which the exact amount of hydrogen gas necessary to maintain catalyst activity will be readily obvious to one skilled in the art from this disclosure, the process under the conditions described herein can be continuously maintained without significant catalyst deactivation.

Meta-cresol as the phenolic compound was also run substantially under the above-described conditions using molybdenum sulfide catalyst yielding toluene.

What is claimed is:

1. A process for dehydroxylating a phenolic compound comprising contacting said phenolic compound or mixture thereof in the vapor phase with a reducing atmosphere substantially comprising hydrogen sulfide, as the reducing agent, in the presence of a sulfur-tolerant metal sulfide catalyst at elevated temperature, wherein said atmosphere further comprises from about 0.001 to about 15 volume percent hydrogen gas.

2. The process of claim 1 wherein said hydrogen gas is present in a sufficient amount to maintain catalyst activity.

3. The process of claim 1 wherein said atmosphere comprises from about 0.5 to about 4 percent hydrogen gas.

4. The process of claim 1 wherein said catalyst is molybdenum sulfide, niobium sulfide, iron sulfide, cobalt sulfide, tungsten sulfide, nickel sulfide or mixtures thereof.

5. The process of claim 4 wherein said catalyst is niobium sulfide.

6. The process of claim 1 wherein said catalyst is supported on a difficultly sulfidable metal oxide.

7. The process of claim 6 wherein said support is gamma-alumina.

8. The process of claim 1 wherein said phenolic compound is a mono-, di- or trihydroxy derivative of benzene; mono-, di- or trialkylbenzene; naphthalene, and mono-, di- or trialkylnaphthalene, or mixture thereof.

9. The process of claim 8 wherein said phenolic compound is phenol, cresol, xylenol, or mixtures thereof.

10. The process of claim 1 wherein said phenolic compound comprises the liquid phenolic component of a naphtha fraction in a coal liquid formed by the pyrolysis or direct liquefaction of coal.

11. The process of claim 1 wherein the volume ratio of said reducing atmosphere to phenolic compound in the vapor phase is about 3:1 to 200:1.

12. The process of claim 1 conducted at a temperature of about 200° to 600° C.

13. The process of claim 1 conducted at a pressure of about 0.1 to 2.0 MPa.

14. The process of claim 1 conducted at a space velocity of about 100 to 10,000 v/v/hr.

15. The process of claim 1 conducted in a continuous manner.

16. A process for dehydroxylating the phenolic components in a naphtha fraction of a coal liquid formed by the pyrolysis or direct liquefaction of coal comprising contacting said phenolic naphtha fraction with a gaseous hydrodesulfurization unit effluent comprising 90 to 40 volume percent hydrogen sulfide and 10 to 60 volume percent hydrogen, in the presence of a sulfur-tolerant metal sulfide catalyst at elevated temperature.

* * * * *